United States Patent [19]
Janick et al.

[11] 4,301,619
[45] Nov. 24, 1981

[54] PLANT TISSUE PRODUCED BY NON-AGRICULTURAL PROLIFERATION OF CACAO EMBRYOS

[75] Inventors: Jules Janick; Valerie C. Pence, both of West Lafayette, Ind.

[73] Assignee: Purdue Research Foundation, West Lafayette, Ind.

[21] Appl. No.: 111,196

[22] Filed: Jan. 11, 1980

Related U.S. Application Data

[63] Continuation-in-part of Ser. No. 951,267, Oct. 13, 1978, Pat. No. 4,204,366.

[51] Int. Cl.³ .............................................. A01G 1/00
[52] U.S. Cl. ......................................................... 47/58
[58] Field of Search ............................................ 47/58

[56] References Cited

U.S. PATENT DOCUMENTS 4,204,366   5/1980   Janick ..................................... 47/58

*Primary Examiner*—Robert E. Bagwill
*Attorney, Agent, or Firm*—John R. Nesbitt

[57] ABSTRACT

This invention is a non-agricultural method for producing cotyledons of those plant species whose cotyledons have commercial value for the manufacture of useful products or for direct use as foodstuffs such as *Theobroma cacao* L. (cacao). The method involves three (3) distinct steps, namely, (1) proliferation of embryos by asexual embryogenesis through in vitro culture using a defined media; (2) the growth of the embryos in vitro in a media that will prevent premature germination, and (3) harvest of the in vitro-grown cotyledonary tissue.

2 Claims, 1 Drawing Figure

PLANT TISSUE PRODUCED BY NON-AGRICULTURAL PROLIFERATION OF CACAO EMBRYOS

RELATED APPLICATION

This application is a continuation-in-part of our co-pending U.S. patent application Ser. No. 951,267, filed Oct. 13, 1978 and entitled "A Method of Non-Agricultural Production of Cotyledons (now U.S. Pat. No. 4,204,366)."

This invention relates to a living plant tissue which is produced by in vitro culture of embroys of cacao.

BACKGROUND OF THE INVENTION

A research report by Brent H. Tisserat, Edward B. Esan and Toshio Murashige entitled "Asexual Embryogenesis in Angiosperms" is the most recent and exhaustive report on asexual embryogenesis in vitro known to applicants.

A section of that report states:
"Table 2 lists the plants, the tissue cultures of which have been reported to generate asexual embryos."

Their Table 2 purports to be a complete survey and does include a few cotyledoneous explants, but there is at least one significant omission, namely, cacao, and a further section of the report, entitled "Morphological Aspects of Asexual Embryogeny in Vitro" makes it apparent that the authors have described the current state of the art solely in terms of its agricultural impact, namely, the aspect of plant reproducibility, and not in any sense have they related embryogenesis to the use to which it is put by applicants.

The authors state their conclusion to be:
"Asexual embryogenesis might be viewed as reflecting a failure of normal development. Nevertheless, it has practical agricultural significance. It enables clonal propagation of some species. The plants derived through asexual embryogeny are often free of many pathogens, especially viruses, that might have infected the original plant (Bitters, et al., 1970). Its manifestations in tissue cultures might be used advantageously in clonal multiplication of cultivars that are currently propagated by seeds. We foresee in the very near future clonal seeds from asexual embryos produced in vitro.

The naturally highly polyembryogenic situation has been an obstacle in plant breeding, since it is usually difficult, if not impossible, to distinguish and separate the zygote embryo from the asexual embryos. Methods are needed to enable separation of the two kinds of embryo or to selectively suppress development of the asexual ones."

THE DRAWINGS

FIG. 1 is a graphic representation comparing a known cocoa butter standard against an asexually produced embryo produced according to the present invention.

SUMMARY OF THE INVENTION

The entire history of agriculture and horticulture has been the field or greenhouse growth and cultivation of various plants for their parts, usually fruits and seeds.

With world population and food needs on an inexorable increase, a new method for production of foodstuffs is needed, and is here proposed.

To achieve the present invention it is necessary for the horticulturist or agronomist to divorce himself from the current state-of-the-art described above, and to recognize that in the production of certain commercial crops, for example, cacao, what is desired from the commercially grown crop is not the complete cacao tree, nor even the whole cacao bean. What is desired is a massive quantity of the stuff of which the cotyledons of such seeds are largely composed. Once this recognition is made, the techniques of embryogenesis may be put to work. The applicants have proved that, given the right conditions, embryogenesis of cacao can be obtained.

DETAILED DESCRIPTION OF THE PREFERRED EMBODIMENT OF THE INVENTION

Cacao

Figure 1:
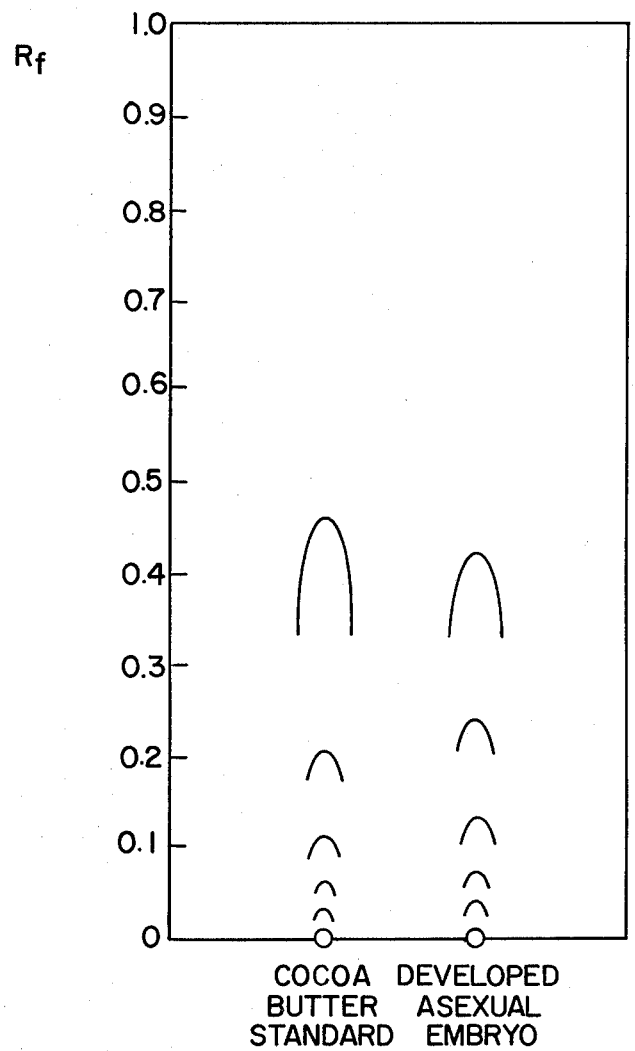

*Theobroma cacao*, grown extensively in portions of Africa and South America for the production of cocoa and chocolate, is normally propagated by seed. Typically a small percentage of trees produce the majority of the crop, and thus vegetative propagation of high-yielding clones is desirable. Normal trees can be obtained from cuttings of upright branches, but they are limited in number; cuttings from the numerous fan branches produce structurally inferior trees. The traditional agricultural approach suggests propagation through tissue culture might provide a superior alternative to seed or vegetative propagation by cuttings, allowing for rapid production of large numbers of desirable clones. However, cacao regeneration through tissue culture has not yet been reported. Cacao callus has been successfully grown from various tissue, including cambium (Archibald, 1954), seedling root, stem, hypocotyl or cotyledon (Hall and Collin, 1975), leaf and fruit (Searles, et al., 1976), embryo and somatic tissue of anthers (Prior, 1977). The development of organized structures from callus has been limited to roots (Hall and Collin, 1975).

This invention does not relate to the potential of cacao for regeneration in tissue culture for the production of superior plants. Nevertheless, the same approaches were used to produce the results of this invention that are used by investigators attempting to produce new plants.

Methods and Results

The basal medium used for in vitro propagation of cacao is as follows:

The Murashige and Skoog (1962) salts (M & S Salts) 100 mg/liter inositol, 0.5 mg/liter nicotinic acid, 2.0 mg/liter glycine, 0.1 mg/liter thiamine HCl, 0.5 mg/liter pyridoxine HCl, 2 g/liter casein hydrolysate, 30 g/liter sucrose, and 10 g/liter agar.

Immature zygotic embryos (2.5 to 10 mm) of Amelonado cacao cultured in the dark on the basal medium in the presence of a growth enhancer such as, for example, 1.5 mg/liter naphthaleneacetic acid (NAA) and 100 ml/liter of deproteinized coconut water, resulted in asexual proliferation of new embryos on 2 out of 10 embryos cultured in the dark and 5 out of 8 embryos cultured in the light.

Two distinct types of embryo development were observed, both of which occurred in the same cotyledon. In the first type, portions of the cotyledons became swollen and green and folded until embryo axes with cotyledons were formed. In the other type, green swellings appeared, usually at the edge of a cotyledon, and from these swellings new embryos "budded." These buds appeared to progress through the normal developmental stages of the cacao embryo described by Cheesman (1927) to the point at which the embryo appears to be at the same developmental stage as a normal 100-120 day in vivo embryo.

Asexual embryos, when transferred at this stage to liquid basal medium which is free of NAA and coconut water and rotated gently (50 rpm) on a rotary shaker, continue to develop into a mature embryo which were morphologically normal. Fresh weight of these embryos was equivalent to in vivo grown seeds. The cotyledons become thickened and folded, but are not as tightly compressed as those in vivo as they are not under the constraints of the seed coat.

In an experiment designed to determine the prevalence of asexual embryogenesis five genotypes were cultured on the same media and all proliferated embryos. All the three cultivars (Amelonado, UF 221 and 41R) with embryos about 2-4 mm long (100-120 day stage) proliferated in at least 80% of the cotyledons in three weeks; proliferation in SIAL 93 and UF 11 where embryos were larger (10-15 mm) had proliferation frequencies of 47% and 38%, respectively.

The plant tissues produced by the method described herein above and a known standard of cocoa butter were examined by means of thin layer chromatography. FIG. 1 shows the results, wherein the $R_f$ values obtained are plotted for the cocoa butter standard (on the left) and for a plant tissue produced by the teaching of this invention (on the right). Specifically, what is shown is the $R_f$ values obtained by use of a thin layer chromatographic plate which was pretreated with 12.5% silver nitrate using a solvent system of chloroform:benzene:ether in the ratio of 70:30:0.05.

It will be noted that the metabolite products are comparable, though not identical. This demonstrates both the utility of the present invention, namely, that the cotyledons of asexually produced embryos according to the methods described produce precursors for useful products, such as cocoa butter, and also that the particular product produced is not identical to the known cocoa butter standard. The latter point suggests that further work is needed to show, develop and mature cacao embryos such as are produced according to this invention to actually obtain a product identical to that produced by normal agricultural methods.

Conclusion

These experiments demonstrate that immature sexual embryos of *T. cacao* proliferate asexual embryos in the basal media described containing coconut water and NAA, and grow. Embryogenesis of cacao has never been observed in various studies of our own and of others using any other tissue.

Cacao is a crop grown specifically for the cotyledon. The produce of commerce in cacao is obtained when mature seeds are removed from the pods, fermented and dried. These are then shipped to the consuming nations, where they are roasted to produce cocoa and chocolate.

The present invention teaches a system in which cacao cotyledons are produced in large numbers in vitro.

This invention teaches a method whereby cacao cotyledons are produced in vitro under controlled conditions. Such a process may also have application with embryos from other species grown for cotyledonous products such as in edible beans, nuts or oil producing plants such as jojoba.

What is claimed:

1. Cotyledonary tissues of asexual embryos produced by the following steps:
   (A) proliferation of immature zygotic cacao embryos in a basal medium in the presence of a growth enhancer whereby asexual embryos are initiated upon said zygotic embryos; and
   (B) growing said asexual embryos in vitro in a basal medium;
   (C) harvesting the cotyledonary tissue of said asexual embryos.

2. An asexual embryo capable of forming cotyledonous tissue produced by the following steps:
   (A) proliferation of immature zygotic cacao embryos in a basal medium in the presence of a growth enhancer whereby asexual embryos are initiated upon said zygotic embryos; and
   (B) growing said asexual embryos in vitro in a basal medium.

* * * * *